(12) United States Patent
Nelson et al.

(10) Patent No.: US 7,482,486 B2
(45) Date of Patent: Jan. 27, 2009

(54) METHODS FOR THE PREPARATION AND FORMULATION OF MAGNESIUM VALPROATE HYDRATE

(75) Inventors: Deanna Jean Nelson, Cary, NC (US); Walter Charles Holberg, III, Apex, NC (US)

(73) Assignee: BioLink Life Sciences, Inc., Cary, NC (US)

( * ) Notice: Subject to any disclaimer, the term of this patent is extended or adjusted under 35 U.S.C. 154(b) by 398 days.

(21) Appl. No.: 11/246,777

(22) Filed: Oct. 7, 2005

(65) Prior Publication Data

US 2007/0083063 A1    Apr. 12, 2007

(51) Int. Cl.
*C07C 53/00*    (2006.01)

(52) U.S. Cl. .................................................... 562/606
(58) Field of Classification Search .................... None
See application file for complete search history.

(56) References Cited

U.S. PATENT DOCUMENTS

| 4,988,731 | A | * | 1/1991 | Meade | 514/557 |
| 5,180,850 | A | * | 1/1993 | Cavazza | 562/606 |
| 6,753,349 | B1 | * | 6/2004 | Weh | 514/557 |

* cited by examiner

*Primary Examiner*—Deborah D Carr

(57) ABSTRACT

The present invention relates to methods for preparing magnesium valproate hydrate and administering this compound to a subject in need of treatment with valproate. Pharmaceutical compositions are also provided that are useful therapies for the treatment of neurological, immunological, and viral-mediated disorders in warm-blooded mammals.

16 Claims, No Drawings

METHODS FOR THE PREPARATION AND FORMULATION OF MAGNESIUM VALPROATE HYDRATE

CROSS-REFERENCE TO RELATED APPLICATIONS

None.

STATEMENT REGARDING FEDERALLY SPONSORED RESEARCH & DEVELOPMENT

No Federally sponsored research & development was used in making this invention.

FIELD OF THE INVENTION

The present invention relates to methods for preparing magnesium valproate hydrate and administering this compound to a subject in need of treatment with valproate. Pharmaceutical compositions are also provided that are useful therapies for the treatment of neurological, immunological, and retroviral-mediated disorders in warm-blooded mammals.

BACKGROUND OF THE INVENTION

Valproic acid (Chemical Abstracts Service (CAS) Registry No. 99-66-1) is a branched carboxylic acid having the molecular formula $C_8H_{16}O_2$. Valproic acid is also known as 2-propylpentanoic acid, 2-propylvaleric acid, and dipropylacetic acid. Valproic acid is a colorless liquid having a boiling point of 120-121° C. at 14 torr. The compound is very slightly soluble in water. It has a pKa of 4.6, and reacts with bases to form salts generally known as valproates.

Clinical Uses

Valproic acid (valproate) has been approved by regulatory agencies around the world, including the U.S. Food and Drug Administration (FDA), as a therapy for several clinical indications, including neurological disorders, mania, manic episodes associated with bipolar disorder, epilepsy, and affective and attention deficit disorders. In addition, valproate is used for the prophylactic treatment, modulation and management of migraine headache, chronic pain, and neuropathic pain.

Further, potential therapeutic benefits of valproate in still other clinical indications are being evaluated in on-going clinical trials. Valproate therapy is being evaluated in clinical studies assessing activity of the substance as a histone deacetylase inhibitor to promote cell differentiation and regeneration, or to regulate gene expression in subjects afflicted with spinal muscular atrophy. Likewise, valproate may exhibit therapeutic benefit as a combinatorial therapeutic treatment of human cancers and for the treatment of tumor metastasis. Similarly, valproate may be useful in the treatment and management of pain, for treating severe tinnitus, for treatment of disorders of personal attachment and deficient social interaction, or for treating Alzheimer's disease. Preclinical studies also show that valproate may promote neural stem cell differentiation and or be useful as a co-medicament to promote the elimination of the Human Immunodeficiency Virus (HIV) or other retroviruses from the body or to prevent progression of a retroviral infection to AIDS.

Sources of the Active Pharmaceutical Ingredient Valproate

Although valproate is a therapeutically active pharmaceutical ingredient, valproic acid is an oil that is difficult to formulate and use in the preparation of dosage forms suitable for human or veterinary use. In addition, the administration of valproic acid to subjects requiring its therapeutic administration results in the exhibition of deleterious side effects, including gastrointestinal distress and ulceration. Pharmaceutical and pharmacological advantages are gained when therapeutic dosage forms are prepared from alkali metal or alkaline earth metal salts of valproic acid. Therefore, alkali metal or alkaline earth metal salts of valproic acid are used in present-day clinical formulations as sources of the active drug ingredient, valproate.

Sodium ($Na^{1+}$), calcium ($Ca^{2+}$) and magnesium ($Mg^{2+}$) valproates have been evaluated for use in pharmaceutical and veterinary compositions. Sodium valproate is a hygroscopic salt that is difficult to formulate into pharmaceutical formulations. In contrast, non-stoichiometric valproate sodium compounds comprising combinations of sodium valproate and valproic acid (divalproex sodium, for example) are not hygroscopic, and are bioavailable and therapeutically active sources of valproate. (The non-stoichiometric compound known as divalproex sodium is disclosed in U.S. Pat. No. 4,988,731, for example, and one of its therapeutic embodiments is described in the FDA Approved Labeling Text for NDA 21-168, Aug. 4, 2000.) At the present time, divalproex sodium is the most commonly formulated source of the drug valproate.

Calcium valproate has also been evaluated for use in pharmaceutical and veterinary formulations. Methods for the preparation of calcium salts of valproic acid are disclosed in U.S. Pat. No. 4,895,873. Although pharmaceutical formulations comprising calcium valproate have been approved by the regulatory bodies of several countries, the use of this valproate salt has been severely restricted following publication of reports of adverse toxicological and reproductive effects in dogs, rats, mice, rabbits, and rats. (For example, adverse effects caused by calcium valproate administration are reported in "Calcium valproate-induced uterine adenocarcinomas in Wistar rats" by Watkins, Gough, et al. in Toxicology, Vol. 41, pages 35-47, 1993.)

Magnesium valproate is also used in clinical formulations. Magnesium valproate, which has the CAS Registry No. 6285-943-7, a molecular formula of $C_{16}H_{30}O_4Mg$, and a molecular weight of 310.71, is also known as magnesium 2-propylvalerate and as 2-propylpentanoic acid magnesium salt. By weight, its composition is 61.8% carbon, 9.7% hydrogen, 7.8% magnesium, and 20.6% oxygen.

Clinical investigators have reported that magnesium valproate possesses pharmacokinetic properties comparable to sodium valproate or valproic acid, is hydrolyzed to valproic acid and magnesium ions upon absorption in the bloodstream, and has important advantages in comparison with either sodium valproate or valproic acid. Among the therapeutic advantages of magnesium valproate are the clinical observations that magnesium valproate exhibits a slower and more regular absorption rate, which prevents the variations in plasma levels of valproate typically observed when sodium salts of valproic acid are administered. Additional therapeutic benefits are afforded by magnesium ions, which possess anticonvulsant and sedative properties. [X. Rabasseda, Drugs of Today, Vol. 31, No. 3, 1995, pp. 185-190.] In contrast to calcium valproate, which exacerbates malignancy, magnesium valproate is a useful therapy when administered to patients with cervical cancer. For example, Chavez-Blanco et al. have reported that magnesium valproate at a dose between 20 and 40 mg/kg inhibits deacetylase activity and hyperacetylates histones in tumor tissues. [A. Chavez-Blanco, B. Segura-Pacheco, et al., Molecular Cancer Jul. 7, 2005, Vol. 4, pp. 22ff.]

In spite of the therapeutic benefits of magnesium valproate, this valproate salt is used less frequently than other valproates in pharmaceutical and veterinary formulations. One reason is the difficulty in preparing the magnesium salt having the formula $C_{16}H_{30}O_4Mg$ with physicochemical properties suited to pharmaceutical applications. The known methods for its preparation suffer from deficiencies in pharmaceutical manufacturing utility and provide magnesium valproate lacking the purity, solubility, and physicochemical properties which enable its use in pharmaceutical formulations for human clinical or veterinary use.

Spanish Patent No. ES 430062 discloses one method for the preparation of magnesium valproate in which valproic acid is allowed to react with magnesium oxide in alcoholic medium. The method has the following shortcomings. The reaction is carried out in a suspension. Reaction times are lengthy. The final product is contaminated with unreacted magnesium oxide, which commingles with the desired product when acetone is added to precipitate the magnesium valproate. The resulting product is an amorphous solid that is difficult to purify and dry. The product has poor bioavailability.

In U.S. Pat. No. 5,180,850 to Cavazza, a method is disclosed for the preparation of crystalline magnesium valproate. (The same procedure is disclosed in Italian Patent No. 2,283,789 and in EP 433,848 B1.) According to the method of Cavazza, valproic acid is reacted with a substantially stoichiometric amount of a magnesium alkoxide selected from magnesium ethoxide, magnesium propoxide, and magnesium isopropoxide in methanol or ethanol. The magnesium salt of valproic acid is isolated in a microcrystalline form by solvent evaporation or by acetone precipitation. The method has the following shortcomings. Product isolation by solvent evaporation provides product that is contaminated by incompletely reacted starting materials or adventitious contaminants in starting materials or solvents. When the reaction is carried out in ethanol, the quantity of magnesium ethoxide specified is not completely dissolved in the volume of ethanol taught. Although some conversion to magnesium valproate occurs, the method does not permit control of temperature, reaction time, removal of impurities, etc. When the reaction is carried out in methanol, the addition of acetone fails to precipitate the product, using the volume of acetone taught in the patent.

In U.S. Pat. No. 6,753,349, Weh discloses a method for producing compositions containing at least one molecule of a valproic acid salt and at least one molecule of valproic acid. The valproic acid salt represents an alkali or alkaline earth salt of valproic acid, wherein the alkali salt is a valproate salt of lithium, sodium, potassium, or rubidium, and the alkaline earth salt of valproic acid is a valproate salt of magnesium, calcium, strontium, or barium. Preferably, the valproate salt is a sodium, potassium, magnesium or calcium salt. The compounds of Weh's invention have the general formula:

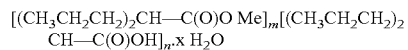
[(CH$_3$CH$_2$CH$_2$)$_2$CH—C(O)O Me]$_m$[(CH$_3$CH$_2$CH$_2$)$_2$CH—C(O)OH]$_n$·x H$_2$O in which Me is $Li^{1+}$, $Na^{1+}$, $K^{1+}$, $Rb^{1+}$, $Mg^{2+}$, $Ca^{2+}$, $Sr^{2+}$, or $Ba^{2+}$, preferably $Na^{1+}$, $K^{1+}$, $Mg^{2+}$, or $Ca^{2+}$; m is an integer from 1 to 10, preferably from 1 to 6, n is an integer from 1 to 9, preferably from 1 to 3, and the ratio m:n is from 1:1 to 6:1, preferably 1:1 to 5:3 and particularly preferably 1:1, 4:3, or 2:1; and x is zero, 1 or 2, preferably zero or 1. In general, the method of preparing magnesium valproate compositions of Weh's invention comprises combining a selected amount of magnesium carbonate, magnesium bicarbonate, or combinations thereof with a selected amount of valproic acid to form a reaction mixture; and allowing the valproic acid to react directly with the magnesium carbonate, magnesium bicarbonate, or combinations thereof under conditions where the reaction temperature is controlled above the melting point of valproic acid. The methods exhibit the following shortcomings. Neither U.S. Pat. No. 6,753,349 nor related international patents WO 2001/032595 and EP 1,230,205 B1 disclose methods for the preparation of each of the several magnesium valproate compositions that are disclosed in these patents. In the absence of data disclosing the ratios of magnesium carbonate and/or magnesium bicarbonate that must be employed to obtain one of the several magnesium valproate compositions that are disclosed by Weh, a knowledgeable artisan must undertake extensive experiments in order to define a process suitable for pharmaceutical manufacturing. Further, valproic acid is an oil and not a solid with a known melting point, so omission in the disclosure of an optimal reaction temperature also requires extensive experimentation. The final product is contaminated with unreacted magnesium carbonate or bicarbonate, as well as other magnesium valproate salts, all of which commingle with the desired product. No methods for product purification are disclosed. The bioavailability of Weh's magnesium valproate compositions is not reported.

In brief, clinicians have shown that magnesium valproate is a useful source of the drug valproate that provides therapeutic benefits and an absence of adverse effects commensurate with or exceeding those observed when valproic acid, sodium valproate compositions, and other valproate salts are used as a source of valproate. To date, however, significant shortcomings in preparative methods have prevented broader therapeutic applications of magnesium valproate. The present invention remedies these shortcomings.

DETAILED DESCRIPTION OF THE INVENTION

The present invention relates to methods for preparing solutions of magnesium valproate in alcoholic solvents and recovering magnesium valproate hydrate therefrom. Magnesium valproate hydrate is a bioavailable source of valproate, a drug that is useful for several clinical indications, including neurological disorders, including mania, manic episodes associated with bipolar disorder, epilepsy, and affective and attention deficit disorders. In addition, valproate is used for the prophylactic treatment, modulation and management of migraine headache, chronic pain, and neuropathic pain.

The present invention also relates to a method of formulating magnesium valproate hydrate in solid dosage forms or in water or aqueous solutions in concentrations that provide a therapeutically effective amount of valproate to a warm-blooded animal after the formulation is administered to the animal.

The present invention provides magnesium valproate hydrate, a heretofore unknown valproate salt. A CAS Registry Number has not yet been assigned to this substance. The molecular formula of magnesium valproate hydrate is $C_{16}H_{30}O_4Mg \cdot x\ H_2O$, wherein x has a value of about 0.7. By weight, its composition is 59.4% carbon, 9.8% hydrogen, 7.5% magnesium, and 23.3% oxygen. Magnesium valproate hydrate is about 88.6% valproate by weight. Also within the scope of this invention are magnesium valproate hydrate compositions having specific bulk densities or tap densities, and magnesium valproate hydrate compositions having specific particle sizes. Further included within the scope of this invention are magnesium valproate hydrate compositions coated with pharmaceutically acceptable materials intended to modify the release and/or bioavailability of the magnesium valproate hydrate (e.g., Eudragit, microcrystalline cellulose, hydroxypropylmethylcellulose phthalate, and so forth).

According to the methods of the present invention, magnesium valproate hydrate is administered, alone or in combination with other therapeutically active or inactive substances, as a therapeutically effective and biologically available (i.e., bioavailable) source of magnesium ions and valproate that are useful for the treatment of neurological, immunological, and viral-related disorders.

The term "excipient material" means any compound forming a part of the formulation, which is not intended to have independent biological activity, and which is added to a formulation to provide specific characteristics to the dosage form, including providing protection to the active ingredient from chemical degradation, facilitating release of a tablet or caplet from the contact surfaces of manufacturing equipment, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms or conditions.

The phrase "therapeutically effective" is intended to qualify the amount of magnesium valproate hydrate for use in the orally or intravenously administered therapy which will achieve the goal of providing a biologically available (i.e., bioavailable) concentration of the drug valproate to effect reducing or preventing, for example, a neurological, immunological, or viral-related disorder, while avoiding adverse side effects typically associated with valproic acid, sodium valproate compositions, or other valproate salts.

Included within the scope of this invention is a method of treating neurological disorders, immune disorders, or viral-related disorders in a warm-blooded animal using pharmaceutical compositions comprising magnesium valproate hydrate, a linear or branched alcohol having from 1 to about 6 carbon atoms, or an organic polyol having from 2 to 100 hydroxyl groups, and a suitable pharmaceutical carrier.

For the purpose of this disclosure, a warm-blooded animal is a member of the animal kingdom which includes but is not limited to mammals and birds. The most preferred mammal of this invention is human.

Surprisingly, the inventors have discovered methods for the preparation of a heretofore unknown valproate salt, magnesium valproate hydrate, that afford significant advantages, particularly in pharmaceutical manufacturing and formulation. For example, magnesium valproate hydrate of the present invention, a white solid, is recovered in high yields from alcohol solutions containing magnesium valproate by the addition of a non-oxygen-containing organic solvent having a boiling point less than about 130° C. in a volume sufficient to reduce the solubility of magnesium valproate in the resulting reaction mixture to less than about 10 mg/mL. The magnesium valproate hydrate solid thus obtained has high purity, is free of contaminating inorganic and organic magnesium salts and residual solvents, is not hygroscopic or deliquescent, and is stable during storage. Further, the magnesium valproate hydrate of the present invention readily dissolves in water or aqueous solutions to provide aqueous solutions having a valproate concentration in the range from about 10 mg/mL to about 150 mg/mL and near neutral pH.

Alcoholic solutions of magnesium valproate were prepared according to the present invention using well-known and commercially available reagents. The alcoholic solvent was methanol, ethanol, propanol, 2-propanol, or a mixture thereof. The alcoholic solvent was selected to dissolve a specific mass of magnesium valproate in the minimum volume of alcoholic solvent that is needed to obtain complete dissolution of either a known mass of magnesium valproate solid or the theoretical mass of magnesium valproate that was obtained by reaction of valproic acid or sodium valproate with a magnesium salt. Magnesium valproate is most soluble in methanol, less soluble in ethanol, and even less soluble in propanol, 2-propanol, or a mixture of alcohols. Therefore, to minimize the volume of alcoholic solvent that is required to obtain a solution of magnesium valproate, methanol and ethanol are preferred. Because recovery of magnesium valproate hydrate of the present invention from methanol solutions was less quantitative than recovery from ethanol solutions, ethanol is most preferred.

Alcoholic solutions of magnesium valproate were prepared according to the present invention in a number of ways. For example, impure magnesium valproate was dissolved in an alcoholic solvent at ambient temperature or at temperatures near the boiling point of the alcohol. When dissolution was completed, the magnesium valproate in solution was purified by treating the solution with decolorizing carbon to reduce the concentration of colored impurities and filtering to remove insoluble substances.

Alternatively, the inventors have discovered that solutions of magnesium valproate are prepared according to the present invention by reacting valproic acid and magnesium methoxide in stoichiometric proportions in an alcoholic solvent. This method of preparation has the advantage that clear and colorless methanol solutions of magnesium methoxide are commercially available. The alcoholic solvent was methanol, ethanol, propanol, 2-propanol, or a mixture thereof.

Likewise, solutions of magnesium valproate were prepared according to the present invention by reacting sodium valproate and a magnesium halide in stoichiometric proportions in an alcoholic solvent. The alcoholic solvent was methanol, ethanol, propanol, 2-propanol, or a mixture thereof. Methanol or ethanol was preferred, and ethanol was most preferred. The sodium halide by-product of reaction is not soluble in alcohol and was removed by filtration to provide an alcoholic solution of magnesium valproate.

Alternatively, solutions of magnesium valproate were prepared by reacting magnesium ethoxide and a 1% to 10% stoichiometric excess of valproic acid in an alcoholic solvent. If magnesium ethoxide is freshly prepared by reaction of magnesium metal with ethanol, for example, a stoichiometric excess of valproic acid of 1% to 3% is sufficient to ensure complete reaction of the freshly prepared magnesium ethoxide with valproic acid. Conversely, if commercially sourced magnesium ethoxide solid was used, a stoichiometric excess of valproic acid of 5% to 10% was required to ensure complete reaction of the magnesium ethoxide with valproic acid, thus providing magnesium valproate in solution. In addition, commercially sourced magnesium ethoxide solid frequently contains colored impurities, and the methods of preparing alcoholic solutions of magnesium valproate of the present invention afford the advantage that the concentrations of colored impurities were reduced by treating the magnesium valproate solution with decolorizing carbon and then removing the particulate by filtration.

Surprisingly, the inventors have discovered that a heretofore unknown valproate salt, magnesium valproate hydrate, a white solid having the molecular formula $C_{16}H_{30}O_4Mg \cdot xH_2O$, is recovered in high yields from an alcoholic solution of magnesium valproate by adding a polar, non-oxygen-containing organic solvent having a boiling point of about 130° C. or lower in a volume sufficient to reduce the solubility of the magnesium valproate in the resulting reaction mixture to less than about 0.01 g/mL. The polar, non-oxygen-containing organic solvent is acetonitrile, propionitrile, butyronitrile, or isobutyronitrile. Acetonitrile is most preferred.

Magnesium valproate hydrate of the present invention is a white solid having the molecular formula $C_{16}H_{30}O_4Mg \cdot xH_2O$, where x is about 0.7. By weight, its composition is 59.4% carbon, 9.8% hydrogen, 7.5% magnesium, and 23.3% oxygen. Magnesium valproate hydrate is about 88.6% valproate by weight. X-ray diffraction analysis indicated that magnesium valproate hydrate has a polymorphic structure that is in part crystalline and in part amorphous; the two structural forms are inseparable. Treatment with acetone did not convert magnesium valproate hydrate to a microcrystalline or amorphous structural form of magnesium valproate hydrate or magnesium valproate nor does acetone treatment convert magnesium valproate hydrate to magnesium valproate.

Magnesium valproate hydrate was not converted to a polymeric magnesium salt of valproic acid by dissolution in acetone and a molar excess of valproic acid, in contrast to methods for preparation of the polymeric valproate sodium composition disclosed in U.S. Pat. No. 4,988,731 or the polymeric valproate magnesium compositions disclosed in U.S. Pat. No. 6,753,349.

While not wishing to be bound by any particular hypothesis or theory, the inventors believe that the physicochemical properties of the polar, non-oxygen-containing organic solvent of the present invention act synergistically to induce precipitation of magnesium valproate hydrate from alcoholic solutions of magnesium valproate by several mechanisms. Chelating bonds between the magnesium ion and oxygen atoms of hydroxyl groups of the alcoholic solvents enhance the solubility of magnesium ions and valproate in alcohols The inventors believe that polar, non-oxygen-containing organic solvent may break these chelating bonds between the magnesium ion and oxygen atoms of hydroxyl groups of the alcoholic solvent(s), thereby reducing solubility and leading to precipitation of the magnesium valproate hydrate salt product. Endothermic cooling of the reacted solution as the polar, non-oxygen-containing organic solvent of the present invention is added to the alcoholic solution of magnesium valproate favors precipitation of the magnesium valproate hydrate product. The source of water in the hydrate complex is believed to be trace amounts present in the solvents and reagents or from the atmosphere.

The methods for the preparation of magnesium valproate hydrate that are disclosed herein are advantageously useful in pharmaceutical manufacturing of this valproate salt, as illustrated by way of example, by the following. The raw materials and solvents are commercially available. The reaction conditions enable control of reaction temperature, monitoring of the progress of reaction for extent of completion, in-process testing of the concentration of magnesium valproate that is present in solution and its quality and purity, methods for the removal of impurities, and convenient and high yield steps for the recovery of magnesium valproate hydrate from the solution.

The magnesium valproate hydrate obtained by the methods of the present invention exhibits both the high purity and absence of both solvents and chemical and biological contaminants, qualities qualifying it for use in pharmaceutical formulations. The magnesium valproate hydrate of the present invention is not hygroscopic or deliquescent and is stable during storage. Further, this valproate salt is easily milled or processed into formulary dosage forms using conventional methods and techniques.

In general, the solubilities of magnesium salts of organic acids in water or aqueous solutions vary unpredictably. Surprisingly, the inventors have found that formulations of magnesium valproate in aqueous solution are readily prepared by dissolving magnesium valproate hydrate of the present invention in water or aqueous solutions of an alcohol or polyol. In this manner, clear and colorless aqueous solutions of magnesium valproate are reproducibly obtained, wherein the concentration of valproate in solution is in the range from about 10 mg/mL to about 150 mg/mL. The basis for this unexpected result is the inventors' discovery that the chelating type of interaction between a magnesium ion and the hydroxyl groups of water, alcohols, or polyols enables and facilitates dissolution of magnesium valproate hydrate in aqueous solutions to provide solutions having valproate concentrations in the range from about 10 to about 150 mg/mL.

DOSAGE FORMS. The pharmaceutical compositions of this invention can be administered by any means that effects contact of the active ingredients with the site of action in the body of a warm-blooded animal. For example, the means can be oral, transdermal, by inhalation, or parenteral (i.e., subcutaneous, intravenous, intramuscular or intraperitoneal). Alternatively or concurrently, the means of administration can be by more than one route (e.g., oral and parenteral). A most preferred means of administration is by the oral route (i.e., ingestion).

The active ingredients can be administered by the oral route in solid dosage forms, such as tablets, capsules, and powders, or in liquid dosage forms, such as elixirs, syrups, and suspensions. The pharmaceutical compositions of this invention also can be administered parenterally, in sterile liquid dosage forms. The pharmaceutical composition is preferably made in the form of a dosage unit containing a particular amount of each active ingredient.

In general, the pharmaceutical compositions of this invention can be prepared by conventional techniques, as are described in *Remington's Pharmaceutical Sciences*, a standard reference in this field [Gennaro AR, Ed. *Remington: The Science and Practice of Pharmacy. 20<sup>th</sup> Edition. Baltimore*: Lippincott, Williams & Williams, 2000]. For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tabletted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. The indicated formulations can contain compatible auxiliaries and excipients, such as anti-oxidants, preservatives, stabilizing agents, emulsifiers, salts for influencing the osmotic pressure, and/or buffer substances.

Other adjuvants and modes of administration are well and widely known in the pharmaceutical art.

Pharmaceutical compositions for use in the treatment methods of the invention may be administered in oral form or by intravenous administration. Oral administration of the therapy is preferred. Dosing for oral administration may be with a regimen calling for single daily dose, or for a single dose every other day, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

Clinical Uses of Magnesium Valproate Hydrate

The present invention provides methods for the reproducible preparation of pharmaceutical quality magnesium valproate hydrate as well as methods for its formulation into pharmaceutical dosage forms using conventional pharmaceutical techniques. In addition, the inventors have shown that aqueous solutions of magnesium valproate hydrate are readily prepared to have valproate concentrations in the range from about 10 mg/mL to about 150 mg/mL. Aqueous solutions of magnesium valproate hydrate comprise fully ionized solutions of magnesium ions and valproate ions which, after parenteral administration to a subject, are completely bioavailable. The inventors have also shown that magnesium valproate hydrate is soluble in simulated gastric fluid USP and in simulated intestinal fluid USP. Given.this solubility, the inventors believe that magnesium valproate hydrate, when administered per os to a subject, will exhibit a bioavailability at least about 90% relative to intravenous infusion, a bioavailability that is equivalent to or exceeds that of divalproex sodium. On these bases, therefore, the inventors believe that magnesium valproate hydrate of the present invention will be administered to subjects in need of valproate therapy as a therapeutically effective and biologically available substitute for valproic acid, divalproex sodium, valproate sodium, and other valproate salt compositions.

For example, the inventors believe that magnesium valproate hydrate of the present invention will be substituted for valproic acid, divalproex sodium, valproate sodium and other valproate salt compositions in compositions useful for the. treatment of neurological disorders as disclosed, by way of example, in U.S. Patent Applications 20050095579, 20050090548, 20050090449, 20050075282, 20050070524, and 20050065340, as well as in U.S. Pat. Nos. 6,406,716, 6,323,236, 6,287,598, and 5,945,416 and in international patents EP 1371366 A1, EP 0966967 A3, EP 1158973 B1, WO 2005070461, WO 2005063297, WO 2005051915, WO 2005049040, and WO 2004101603. Further, the inventors believe that magnesium valproate hydrate of the present invention will be substituted for valproic acid, divalproex sodium, valproate sodium and other valproate salt compositions in compositions useful for the treatment of immunological disorders as disclosed, by way of example, in U.S. Patent Applications 20050119261, 20050090553, 20050065596, 20050065173, 20050054091, as well as in U.S. Pat. Nos. 5,506,224 and 5,432,176 and in international patents EP 1529527 A1, EP 1293205 A1, EP 1170008 A1, EP 1301184 B1, WO 2005023179, WO 2005018578, WO 2004113305, WO 2004096216, WO 2004096224, and WO 2004050076. Likewise, the inventors believe that magnesium valproate hydrate of the present invention will be substituted for valproic acid, divalproex sodium, valproate sodium and other valproate salt compositions in compositions useful for the treatment of viral-related disorders as disclosed, by way of example, in the report of Smith [Retrovirology Sep. 19, 2005, 2(1): 56], Cohen [Science Aug. 12, 2005, 309(5737): 999-1000], Lehrman et al. [Lancet Aug. 13, 2005, 366(9485): 549-555], and Ylisastigui et al. [AIDS May 21, 2004, 18(8): 1101-1108].

The following examples present representative compositions of the present invention. The examples are representative of the scope of the invention, and as such are not to be considered or construed as limiting the invention recited in the appended claims.

EXAMPLE 1

Attempted Preparation of Microcrystalline Magnesium Valproate.

Magnesium valproate was prepared in accordance with the procedure disclosed in U.S. Pat. No. 5,180,850. (The same procedure is disclosed in Italian Patent No. 2,283,789 and in EP 433,848 B1.) Magnesium ethoxide (11.4 g; 100 mmol; Sigma Aldrich Chemical Co.) was stirred in 30 mL of absolute ethanol. Although the patent discloses that dissolution occurs in "a short time", dissolution remained incomplete after 24 hours of stirring and heating. Independent experiments established that the solubility of magnesium ethoxide in ethanol is less than 1 mmol/mL. The present methods require complete dissolution of magnesium alkoxides. The teaching of U.S. Pat. No. 5,180,850 is not applicable to the present methods, since the magnesium ethoxide is not soluble in the reaction solution at the recommended concentration.

EXAMPLE 2

Attempted Preparation of Magnesium Valproate.

11.4 g (0.1 mol) of magnesium ethoxide solid was added to a magnetically stirred, clear, colorless solution of valproic acid (28.8 g; 0.2 mol; Sigma Aldrich Chemical Co.) in 25 mL of absolute ethanol. Residual solid was rinsed into the reaction with 5 mL of absolute ethanol to provide a total volume of 30 mL of absolute ethanol. Within 10 minutes, the slurry became very warm to the touch, and the color of the solution phase changed to pale yellow. Complete dissolution of the magnesium ethoxide solid in ethanol was never achieved, but within minutes the solid phase converted from a slurry of a yellow granular solid to a suspension of white solid that was so thick that stirring stopped. 100 mL of acetone was added, and the thick slurry was stirred for 10 minutes. The precipitate was isolated by filtration, washed with fresh acetone, and dried to constant weight. The product, magnesium valproate, was obtained in 66% yield. Elemental analysis (Table 1) indicated that the product was an inhomogeneous mixture of magnesium valproate and other magnesium salts. The theoretical valproate content (%) of magnesium valproate is 92.2%; the valproate content found by HPLC analysis was 78.4%.

TABLE 1

Percent by weight elemental composition of magnesium valproate

|  | C | H | O | Mg |
|---|---|---|---|---|
| Theoretical | 61.8 | 9.7 | 20.6 | 7.8 |
| Found | 51.7 | 8.94 | Not det'd | 10.1 |

EXAMPLE 3

Attempted Preparation of Microcrystalline Magnesium Valproate.

Attempts were made to prepare microcrystalline magnesium valproate in the following manner. To a magnetically stirred, clear, colorless solution of valproic acid (2.88 g; 0.02 mol; Sigma Aldrich Chemical Co.) in 20 mL of 2-propanol was added 10 mL (0.01 mol) of magnesium methoxide solution in methanol (Sigma Aldrich Chemical Co.). A clear, pale yellow solution was obtained. Acetone was added to the alcohol solution in portions; after 100 mL had been added, a clear and colorless solution was obtained; no precipitate formed. The reaction temperature did not change during the addition of acetone.

EXAMPLE 4

Valproate Analysis by HPLC

In the Examples that follow, weight percent valproate was determined by reversed-phase HPLC analysis using the following conditions:
Column: X-Terra Reversed-Phase C18, 5 µM particle size, 4.6 mm i.d.×250 cm length (Waters)
Mobile Phase A: Acetonitrile (ACN):Water:Trifluoroacetic acid (TFA) 10:90:0.1 (v/v/v)
Mobile Phase B: ACN:TFA 100:0.1 (v/v)
Separation Conditions: Isocratic delivery of A and B in a 60:40 volume ratio of A:B
Flow Rate: 1.0 mL/min
Detection Wavelength: 210 nm
Sample Diluent: Water containing 0.1% TFA
Injection Volume: 5.0 µL
Valproate Retention 9.3 minutes Time:
Acquisition Time: 12 minutes Valproate standards with concentrations ranging from 0.05 µg/mL to 0.5 µg/mL were prepared by dissolution of aliquots of valproic acid and analyzed in triplicate to provide a standard curve, which exhibited a linearity, R, of 0.99998. Peak tailing of the valproate response was less than 2.0. Test samples were prepared by accurately weighing approximately 40 mg of sample, quantitatively transferring the solid to a 100-mL volumetric flask and diluting with water containing 0.1% TFA. Sample analyses were completed in triplicate. Relative standard error of analysis was 1% or less.

EXAMPLE 5

Magnesium Analysis.

Approximately 100 mg of sample was weighed into a 150 mL beaker and 100 mL of methanol was added. The slurry was stirred until the solid appeared complete. (Incomplete dissolution before the addition of acid indicates the presence of contaminating magnesium salts.) Then 2 mL of conc. hydrochloric acid was added, and the resulting solution was stirred for about 10 minutes to ensure complete dissolution of all 15 magnesium salts. Twenty-four mL of 1 N sodium hydroxide solution was added, and the resulting solution was stirred for about 1 minute before 5 mL of Ammonium Chloride-Ammonium Hydroxide TS (USP) was added. After an additional minute of stirring, 3 drops of Eriochrome Black T Indicator Solution were added. The resulting pink solution was stirred as 0.1 N EDTA VS (USP) titrant was added dropwise until a blue color was obtained that persisted for at least 30 seconds. Under these conditions, 1 mL of titrant is equivalent to 2.4305 mg of magnesium.

EXAMPLE 6

Preparation of Magnesium Valproate Hydrate of the Present Invention:

A solution of magnesium valproate in absolute ethanol was obtained in the following manner. To a magnetically stirred, clear, colorless solution of valproic acid (3.17 g; 0.022 mol; Sigma Aldrich Chemical Co.) in 25 mL of absolute ethanol was added 1.14 g (0.01 mol) of magnesium ethoxide solid; residual solid was rinsed in with 1 mL of absolute ethanol. Within 60 minutes, a clear, pale yellow solution was obtained; no heating was observed. One milliliter portions of the solution were aliquoted into test tubes, and a second solvent or solution was added in portions. The results of the additions are summarized in Table 2. A 15 mL portion of acetonitrile was added to an equal volume of the ethanol solution of magnesium valproate. A white precipitate formed, which was isolated by filtration, washed with a fresh portion of acetonitrile, and dried to constant mass. The product, magnesium valproate hydrate, was obtained in 89% yield as a white solid, which exhibited an elemental composition identical to that calculated for magnesium valproate hydrate. The product did not melt at temperatures as high as 300° C. The product was not hygroscopic or deliquescent. The theoretical valproate content (weight %) of magnesium valproate hydrate is 88.6%; the valproate content found by HPLC analysis was 88.5%.

TABLE 2

Solvents or Solutions Tested

| Solvent or Solution Added | Volume Added | Observation |
|---|---|---|
| Saturated NaCl solution (brine) | 1 mL | Copious white precipitate |
| Ethyl acetate | 1 mL | Clear solution |
| Acetonitrile | 1 mL | Copious white precipitate |
| Methyl t-butyl ether | 1 mL | Clear solution |
| Tetrahydrofuran | 1 mL | Clear solution |
| Dimethoxyethane | 1 mL | Clear solution |
| Water | 1 mL | Cloudiness and some precipitate |
| Acetone | 5 mL | Clear solution |
| Saturated NaCl solution (brine) | 4 drops | Copious white precipitate |
| Saturated NaHCO$_3$ solution | 4 drops | Copious white precipitate |
| Hexanes | 3 mL | Clear solution |

EXAMPLE 7

Preparation of Magnesium Valproate Hydrate of the Present Invention:

Method A.

A solution of magnesium valproate was obtained in the following manner. To a magnetically stirred, clear, colorless solution of valproic acid (2.88 g; 0.02 mol; Sigma Aldrich Chemical Co.) in 20 mL of 2-propanol was added 10 mL (0.01 mol) of magnesium methoxide solution in methanol (Sigma Aldrich Chemical Co.). A clear, pale yellow solution was obtained. Acetonitrile was added to the alcohol solution in portions, and after 100 mL had been added, a white precipitate formed. The reaction mixture was cold to the touch. The slurry was stirred for 15 minutes. The product, magnesium valproate hydrate, was isolated by filtration, washed with fresh acetonitrile, and dried to constant weight. The product, magnesium valproate hydrate, was obtained in 70% yield as a white solid, which exhibited an elemental composition identical to that calculated for magnesium valproate hydrate. The product did not melt at temperatures as high as 300° C. The product was not hygroscopic or deliquescent and was stable during storage under ambient conditions. The theoretical valproate content (weight %) of magnesium valproate hydrate is 88.6%; the valproate content found by HPLC analysis was 88.5%.

EXAMPLE 8

Preparation of Magnesium Valproate Hydrate of the Present Invention:

Method B.

A solution of magnesium valproate in absolute ethanol was obtained in the following manner. To a magnetically stirred, clear, colorless solution of valproic acid (2.88 g; 0.02 mol; Sigma Aldrich Chemical Co.) in 25 mL of absolute ethanol was added 0.8 g (0.02 mol) of sodium hydroxide solid. Within an hour, a clear, colorless solution was obtained; no increase in reaction temperature was observed. A solution of magnesium chloride hexahydrate (2.03 g; 0.01 mol) in 10 mL of absolute ethanol was added in portions. A white precipitate formed (NaCl). The slurry was stirred for 1 hour to ensure complete reaction, and then filtered to remove the NaCl from the clear, colorless filtrate. A volume of acetonitrile (35 mL) equal to the volume of ethanol used was added to the filtrate in portions, and a white precipitate formed. The reaction mixture was cold to the touch. The slurry was stirred for 15 minutes. The product, magnesium valproate hydrate, was isolated by filtration, washed with fresh acetonitrile, and dried to constant weight. The product, magnesium valproate hydrate, was obtained in 56% yield as a bright white solid, which exhibited an elemental composition identical to that calculated for magnesium valproate hydrate (Table 3). The product did not melt at temperatures as high as 300° C. The product was not hygroscopic or deliquescent and was stable during storage under ambient conditions. X-ray diffraction analysis indicated that magnesium valproate hydrate of the present invention is a polymorph having both crystalline and amorphous structural features. The theoretical valproate content (weight %) of magnesium valproate hydrate is 88.6%; the valproate content found by HPLC analysis was 88.6%.

TABLE 3

Percent by weight elemental composition of magnesium valproate hydrate

| | C | H | O | Mg |
|---|---|---|---|---|
| Theoretical | 59.4 | 9.8 | 23.3 | 7.5 |
| Found | 59.0 | 9.7 | Not det'd | 7.5 |

EXAMPLE 9

Preparation of Magnesium Valproate Hydrate of the Present Invention:

Method C.

A solution of magnesium valproate in absolute ethanol was obtained in the following manner. To a magnetically stirred, clear, colorless solution of valproic acid (31.7 g; 0.22 mol; Sigma Aldrich Chemical Co.) in 200 mL of absolute ethanol was added 11.4 g (0.1 mol) of magnesium ethoxide solid; residual solid was rinsed in with 1 mL of absolute ethanol. Within 30 minutes, a clear, pale yellow solution was obtained; no increase in reaction temperature was observed. Acetonitrile (150 mL) was added to the ethanol solution in portions, and when the addition was complete a white precipitate formed. The reaction mixture was cold to the touch. The slurry was stirred for 15 minutes. The product, magnesium valproate hydrate, was isolated by filtration, washed with fresh acetonitrile, and dried to constant weight. The product, magnesium valproate hydrate, was obtained in 79.8% yield as a white solid, which exhibited an elemental composition identical to that calculated for magnesium valproate hydrate. The product did not melt at temperatures as high as 300° C. The product was not hygroscopic or deliquescent and was stable during storage under ambient conditions. The theoretical valproate content (weight %) of magnesium valproate hydrate is 88.6%; the valproate content found by HPLC analysis was 88.2%.

EXAMPLE 10

Preparation of Magnesium Valproate Hydrate of the Present Invention:

Method D.

Unless magnesium ethoxide is freshly generated in situ by reaction of magnesium metal with ethanol, the magnesium ethoxide solids that are obtained commercially frequently contain colored by-products that are potential contaminants of the desired product, magnesium valproate hydrate. To demonstrate the purification of an alcohol solution containing magnesium valproate and colored contaminants, a solution of magnesium valproate in absolute ethanol was obtained in the following manner. To a magnetically stirred, clear, colorless solution of valproic acid (15.12 g; 0.105 mol; Sigma Aldrich Chemical Co.) in 90 mL of absolute ethanol was added 5.7 g (0.05 mol) of magnesium ethoxide solid (Sigma Aldrich Chemical Co.). Within 30 minutes, a clear, pale yellow solution was obtained; no increase in reaction temperature was observed. The pale yellow solution was treated with decolorizing carbon. After filtration with the aid of Celite to facilitate carbon removal, a nearly colorless filtrate solution was obtained. Acetonitrile (45 mL) was added to the ethanol solution in portions, and when the addition was complete, a white precipitate formed. The reaction mixture was cold to the touch. The slurry was stirred for 15 minutes. The product, magnesium valproate hydrate, was isolated by filtration, washed with fresh acetonitrile, and dried to constant weight. The product, magnesium valproate hydrate, was obtained in 77% yield as a white solid, which exhibited an elemental composition identical to that calculated for magnesium valproate hydrate (Table 4). The product did not melt at temperatures as high as 300° C. The product was not hygroscopic or deliquescent and was stable during storage under ambient conditions. X-ray diffraction analysis showed that magnesium valproate hydrate of the present invention is a polymorph having both crystalline and amorphous structural features. The theoretical valproate content (weight %) of magnesium valproate hydrate is 88.6%; the valproate content found by HPLC analysis was 88.5%.

TABLE 4

Percent by weight elemental composition of magnesium valproate hydrate

| | C | H | O | Mg |
|---|---|---|---|---|
| Theoretical | 59.4 | 9.8 | 23.3 | 7.5 |
| Found | 59.33 | 9.81 | Not det'd | 7.5 |

EXAMPLE 11

Attempted Preparation of Magnesium Valproate.

To a magnetically stirred, clear, colorless solution of valproic acid (3.17 g; 0.022 mol; Sigma Aldrich Chemical Co.) in 20 mL of 2-propanol was added 10 mL (0.01 mol) of magnesium methoxide in methanol solution. A clear, colorless solution was obtained; no increase in reaction temperature was observed. 2-Propanol (45 mL) was added in portions, and when the addition was completed, a white precipitate formed. The white solid contained valproate but did not have a composition corresponding to that of magnesium valproate (Table 5). The theoretical valproate content (weight %) of magnesium valproate hydrate is 88.6%; the valproate content found by HPLC analysis was 41.9%.

TABLE 5

Percent by weight elemental composition of magnesium valproate

| | C | H | O | Mg |
|---|---|---|---|---|
| Theoretical | 61.8 | 9.7 | 20.6 | 7.8 |
| Found | 30.6 | 6.8 | Not det'd | Not det'd |

EXAMPLE 12

Attempted Preparation of Polymeric Magnesium Valproates.

A 3.1 g (0.01 mol) portion of magnesium valproate hydrate (a white solid) was suspended in 40 mL of acetonitrile and 2.88 g (0.02 mol) of valproic acid was added. The suspension was heated at reflux; little dissolution of the solid was observed. Ethanol was added in portions, and the suspension was heated at reflux. After the addition of about 30 mL of ethanol, a clear solution was obtained. The solution was cooled to ambient temperature. A white solid formed, which was removed by filtration. In this manner, about 1.5 g (48%) of magnesium valproate hydrate was recovered. HPLC analysis indicated this material had a valproate content of 89.1%. (The theoretical valproate content of magnesium valproate hydrate is 88.6%.) The concurrence between the valproate content found and the theoretical valproate content confirms that the recovered product was magnesium valproate hydrate.

Volatile solvents were evaporated from the filtrate, and 40 mL of acetone was added to the residual oil. No precipitate formed. No polymeric form of valproate magnesium salt was isolated, in contrast to the polymeric valproate sodium composition disclosed in U.S. Pat. No. 4,988,731 or the polymeric valproate magnesium compositions disclosed in U.S. Pat. No. 6,753,349.

EXAMPLE 13

Preparation of Aqueous Solutions of Magnesium Valproate.

Aqueous solutions of magnesium valproate were prepared in the following manner.

Solution A: 1.10 g of magnesium valproate hydrate of the present invention was dissolved in 10 mL of water. The resulting clear, colorless solution had a valproate concentration of about 100 mg/mL by HPLC analysis.

Solution B: 1.10 g of magnesium valproate hydrate of the present invention was dissolved in 10 mL of 10% poly(ethylene glycol) (average molecular weight of 400 Daltons; i.e., PEG400) in water. The resulting clear, colorless solution had a valproate concentration of about 100 mg/mL by HPLC analysis.

Solution C: 1.10 g of magnesium valproate hydrate of the present invention was dissolved in 10 mL of 10% propylene glycol in water. The resulting clear, colorless solution had a valproate concentration of about 100 mg/mL by HPLC analysis.

Solution D: 1.10 g of magnesium valproate hydrate of the present invention is dissolved in 10 mL of 5% dextrose in water. The resulting clear, colorless solution has a valproate concentration of about 100 mg/mL by HPLC analysis.

EXAMPLE 14

Attempted Preparation of an Aqueous Solution of the Magnesium Valproate of Example 2.

The dissolution of 1.10 g of magnesium valproate that was prepared as described in Example 2 was attempted in 10 mL of water. After 24 hours, dissolution remained incomplete, and undissolved white particles remained visible.

The following examples present hypothetically useful therapeutic uses of representative pharmaceutical compositions of the present invention and their anticipated outcomes in treating neurological diseases in subjects requiring such treatment. The examples are representative of the scope of the invention, and as such are not to be considered or construed as limiting the invention recited in the appended claims.

EXAMPLE 15

Magnesium Valproate Hydrate of the Present Invention in the Treatment of Epilepsy.

The therapeutic benefit of magnesium valproate hydrate of the present invention is compared with that of sodium valproate in an open, comparative clinical trial in epileptic patients. Patients in the study population exhibit symptoms such as tonic-clonic convulsions, tonic nonfocal convulsions, simple absence seizures, absence attacks associated with generalized convulsions, partial convulsions, West syndrome or Lennox-Gastaut syndrome. The study population has previously been treated with sodium valproate (alone or in combination with other drugs) for a minimum of 6 months. Then treatment is substituted with magnesium valproate hydrate (alone or combined with other drugs) for 3 months. The following results are expected to be observed following administration of magnesium valproate hydrate for 3 months. The percentage of patients without convulsions is expected to increase significantly. The number of patients with no convulsions or only occasional convulsions is expected to increase significantly. Patients with generalized nonconvulsive or partial epilepsy are expected to obtain significantly greater therapeutic benefit from treatment with magnesium valproate hydrate rather than sodium valproate, although patients in all other types of epilepsy are expected to obtain equivalent therapeutic benefit from magnesium valproate hydrate or sodium valproate treatment. Patients who receive magnesium valproate hydrate are expected to have fewer side effects (e.g., gastric discomfort or ulceration, malaise).

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The specific embodiments are, therefore, to be construed as merely illustrative, and not limitative of the remainder of the disclosure in any way whatsoever.

We claim:

1. A magnesium valproate hydrate composition, having the molecular formula $C_{16}H_{30}O_4Mg \cdot x\,H_2O$, where x is 0.7, and a weight percent valproate content of about 85% up to about 91%.

2. The composition of claim 1, wherein said magnesium valproate hydrate has a polymorphic structure having both crystalline and amorphous structural properties.

3. A method of obtaining magnesium valproate hydrate from an alcohol solution containing magnesium valproate comprising adding to the alcohol solution a volume of a polar, non-oxygen-containing organic solvent having a boiling point of 130° C. or lower, the volume of said solvent being sufficient to reduce the solubility of the magnesium valproate in the resulting reaction mixture to less than 0.01 g/mL, and isolating the magnesium valproate hydrate from the resulting reaction mixture.

4. The method of claim 3, wherein the alcohol is selected from a group consisting of methanol, ethanol, propanol, 2-propanol, and a mixture thereof and the polar, non-oxygen-containing organic solvent is selected from a group consisting of acetonitrile, propionitrile, butyronitrile, and isobutyronitrile.

5. A method of preparing magnesium valproate hydrate comprising reacting sodium valproate and a magnesium halide selected from a group consisting of magnesium chloride, magnesium bromide, and magnesium iodide in stoichiometric proportions in an alcoholic solvent selected from a group consisting of ethanol and methanol, removing the sodium halide, and recovering magnesium valproate hydrate from the reaction mixture.

6. A method of preparing magnesium valproate hydrate comprising reacting valproic acid and magnesium methoxide in stoichiometric proportions in an alcoholic solvent selected from a group consisting of methanol, ethanol, propanol, 2-propanol, and a mixture thereof, adding to the alcohol solution a volume of a polar, non-oxygen-containing organic solvent having a boiling point of 130° C or lower, the volume of said solvent being sufficient to reduce the solubility of the magnesium valproate in the resulting reaction mixture to less than 0.01 g/mL, and recovering magnesium valproate hydrate from the reaction mixture.

7. A method of preparing magnesium valproate hydrate comprising reacting magnesium ethoxide and valproic acid in 1% 10% stoichiometric excess in an alcoholic solvent selected from a group consisting of methanol, ethanol, propanol, 2-propanol, and a mixture thereof, adding to the alcohol solution a volume of a polar, non-oxygen-containing organic solvent having a boiling point of 130° C or lower, the volume of said solvent being sufficient to reduce the solubility of the magnesium valproate in the resulting reaction mixture to less than 0.01 g/mL, and recovering magnesium valproate hydrate from the reaction mixture.

8. The method of claim 5, 6, or 7, wherein magnesium valproate hydrate is recovered from the reaction mixture by adding a volume of acetonitrile sufficient to cause precipitation of said magnesium valproate hydrate.

9. The method of claim 8, wherein upon adding acetonitrile, the solubility of said magnesium valoroate hydrate is less than about 0.01 g/mL.

10. A method of preparing an aqueous solution of magnesium valproate having a concentration of valproate in the range from about 1 mg/mL to about 150 mg/mL comprising dissolving a known mass of magnesium valproate hydrate in a volume of water sufficient to provide a solution having a valproate concentration in the range from about 1 mg/mL to about 150 mg/mL.

11. A method of preparing an aqueous solution of magnesium valproate having a concentration of valproate in the range from about 1 mg/mL to about 150 mg/mL comprising dissolving a known mass of magnesium valproate hydrate in a volume of a solvent selected from a group consisting of 1-10% dextrose in water, 1-10% poly(ethylene glycol) in water, 1-10% propylene glycol in water, and 1-10% glycerol in water sufficient to provide a solution having a valproate concentration in the range from about 1 mg/mL to about 150 mg/mL.

12. A method of preparing a pharmaceutical formulation of magnesium valproate having a concentration of valproate in the range from about 1 mg/mL to about 150 mg/mL comprising dissolving a known mass of magnesium valproate hydrate in a volume of a solvent selected from a group consisting of water, 1-10% dextrose in water, 1-10% poly(ethylene glycol) in water, 1-10% propylene glycol in water, and 1-10% glycerol in water sufficient to provide a solution having a valproate concentration in the range from about 1 mg/mL to about 150 mg/mL, and optionally, sterilizing the formulation.

13. A method of obtaining magnesium valproate hydrate from a solution of magnesium valproate in a solvent selected from a group consisting of methanol, ethanol, propanol, 2-propanol, and a mixture thereof comprising adding to the solution a volume of acetonitrile sufficient to reduce the solubility of the magnesium valproate in the resulting reaction mixture to less than about 0.01 g/mL, and recovering magnesium valproate hydrate from the reaction mixture.

14. A method of preparing magnesium valproate hydrate comprising reacting sodium valproate and a magnesium halide selected from a group consisting of magnesium chloride, magnesium bromide, and magnesium iodide in stoichiometric proportions in an alcoholic solvent selected from a group consisting of ethanol and methanol, removing the sodium halide, and recovering magnesium valproate hydrate from the reaction mixture by adding a polar, non-oxygen-containing organic solvent selected from a group consisting of acetonitrile, propionitrile, butyronitrile, and isobutyronitrile in a volume sufficient to reduce the solubility of magnesium valproate in the resulting reaction mixture to less than about 10 mg/mL. and recovering magnesium valproate hydrate from the reaction mixture.

15. A method of preparing magnesium valproate hydrate comprising reacting valproic acid and magnesium methoxide in stoichiometric proportions in an alcoholic solvent selected from a group consisting of methanol, ethanol, propanol, 2-propanol, and a mixture thereof, and recovering magnesium valproate hydrate from the reaction mixture by adding a polar, non-oxygen-containing organic solvent selected from a group consisting of acetonitrile, propionitrile, butyronitrile, and isobutyronitnie in a volume sufficient to reduce the solubility of magnesium valproate in the resulting reaction mixture to less than about 10 mg/mL, and recovering magnesium valproate hydrate from the resulting reaction mixture.

16. A method of preparing magnesium valproate hydrate comprising reacting valproic acid in 1%-10% stoichiometric excess and magnesium ethoxide in an alcoholic solvent selected from a group consisting of methanol, ethanol, propanol, 2-propanol, and a mixture thereof, and recovering magnesium valproate hydrate from the reaction mixture by adding a polar, non-oxygen-containing organic solvent selected from a group consisting of acetonitrile, propionitrile, butyronitrile, and isobutyronitrile in a volume sufficient to reduce the solubility of magnesium valproate in the resulting reaction mixture to less than about 10 mg/mL, and recovering magnesium valproate hydrate from the resulting reaction mixture.

* * * * *